United States Patent [19]

Meier et al.

[11] Patent Number: 5,136,043

[45] Date of Patent: Aug. 4, 1992

[54] PROCESS FOR THE PREPARATION OF AROMATIC SULFONYL CHLORIDES

[75] Inventors: Michael Meier, Frankfurt am Main; Wolfgang Tronich, Eppstein, both of Fed. Rep. of Germany

[73] Assignee: Hoechst Aktiengesellschaft, Frankfurt am Main, Fed. Rep. of Germany

[21] Appl. No.: 746,476

[22] Filed: Aug. 16, 1991

Related U.S. Application Data

[63] Continuation of Ser. No. 538,115, Jun. 14, 1990, abandoned.

[30] Foreign Application Priority Data

Jun. 17, 1989 [DE] Fed. Rep. of Germany ....... 3919840

[51] Int. Cl.$^5$ ............................................. C07D 263/58
[52] U.S. Cl. .................................... 548/221; 562/828; 562/830
[58] Field of Search ............................ 562/828, 830, 38; 548/217, 221

[56] References Cited

U.S. PATENT DOCUMENTS

| 2,888,486 | 5/1959 | Gregory | 562/828 |
| 3,686,300 | 8/1972 | Oten et al. | 562/828 |
| 4,316,862 | 2/1982 | Schenk et al. | 562/830 |
| 4,339,396 | 7/1982 | Rauchschwalbe et al. | 562/830 |

FOREIGN PATENT DOCUMENTS

| 1205491 | 6/1986 | Canada. | |
| 0001275 | 4/1979 | European Pat. Off. . | |
| 2928744 | 2/1981 | Fed. Rep. of Germany . | |
| 3302647 | 8/1984 | Fed. Rep. of Germany . | |
| 3306597 | 8/1984 | Fed. Rep. of Germany . | |
| 3501754 | 7/1986 | Fed. Rep. of Germany . | |
| 0077255 | 6/1981 | Japan | 562/830 |
| 0802274 | 2/1981 | U.S.S.R. | 562/828 |
| 1049112 | 6/1989 | U.S.S.R. | 562/828 |
| 1093667 | 12/1967 | United Kingdom | 562/828 |

OTHER PUBLICATIONS

Chem. Abstr. vol. 102 entry 134485v (1985).
"General Characteristics of Benzenesulfonic Acid Derivatives". In: *Ullmann's Encyclopedia of Industrial Chemistry*, 5th Ed., vol. A3, 1986, p. 513.
Bosshard, H. H. et al, *Helv. Chimica Acta* 42: 1653–1658 (1959).
Winnacker-Kuchler, *Chemische Technologie* 6:181–182, Carl Hauser-Verlag Munich Germany (4th ed 1982).
Gmelins *Handbuch der Anorganischen Chemie* 9:1583, Verlag Chemie GmbH, Weinheim, German (1963).

*Primary Examiner*—Donald G. Daus

[57] ABSTRACT

A process for the preparation of aromatic sulfonyl chlorides of the formula I

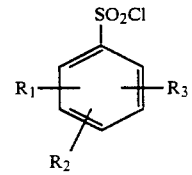

in which $R_1$, $R_2$ and $R_3$ are identical or different and are hydrogen, fluorine, chlorine, bromine or iodine atoms, alkyl($C_1$-$C_4$), acetamido, nitro or carboxyl groups, or $R_1$ and $R_2$ together form an aromatic or heteroaromatic ring having 5 or 6 ring members, which can be substituted by fluorine, chlorine, bromine or iodine atoms, alkyl($C_1$-$C_4$), acetamido, nitro or carboxyl groups, by reaction of aromatic compounds of the formula II

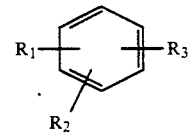

in which $R_1$, $R_2$ and $R_3$ have the abovementioned meanings, with chlorosulfonic acid in excess or with chlorosulfonic acid or oleum and thionyl chloride, by reacting in the presence of sulfamic acid as a catalyst.

6 Claims, No Drawings

PROCESS FOR THE PREPARATION OF AROMATIC SULFONYL CHLORIDES

This application is a continuation of our copending application Ser. No. 07/538,115, filed Jun. 14, 1990, now abandoned.

The invention relates to the preparation of aromatic sulfonyl chlorides in a manner known per se by reaction of aromatic compounds with excess chlorosulfonic acid or with chlorosulfonic acid or oleum and thionyl chloride, the reaction being carried out in the presence of sulfamic acid as a catalyst.

It is known that the sulfonation and sulfochlorination of aromatic compounds can be improved by adding so-called sulfone inhibitors to suppress the sulfone formation observed as a secondary reaction [Ullmann's Encyclopedia of Industrial Chemistry, 5th ed., vol. A.3, p. 513]. Examples of such sulfone inhibitors which may be mentioned are ammonium sulfate, sodium carbonate or potassium carbonate [DE 3,501,754], and sodium chloride or ammonium chloride [DE 3,306,597]. A large number of other sulfonating agents are mentioned in EP 0,001,275.

It is known from Helv. Chimica Acta 42, 1653 (1959) that dialkylformamides act as catalysts in the preparation of naphthalenesulfonyl chlorides from the corresponding sulfonic acids.

Reference is made in DE 2,938,744 to the toxicological problems in the use of dimethylformamide in particular, and substitutes, such as, for example, pyridine, substituted pyridines, tertiary aliphatic amines and quaternary ammonium salts, preferably tertiary amines, are proposed.

The compounds proposed as catalysts or auxiliaries for the sulfonation or sulfochlorination of aromatic compounds are not satisfactory for industrial use, in particular for reasons of occupational hygiene, and thus capable of improvement.

It has now been found that sulfamic acid is a novel, advantageous auxiliary for the sulfochlorination of aromatic compounds to give the corresponding arylsulfonyl chlorides.

The invention thus relates to an improved process, with respect to attainable yields and quality, for the preparation of aromatic sulfonyl chlorides of the general formula I

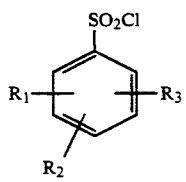

in which $R_1$, $R_2$ and $R_3$ are identical or different and are hydrogen, fluorine, chlorine, bromine or iodine atoms, alkyl($C_1$-$C_4$), acetamido, nitro or carboxyl groups, or $R_1$ and $R_2$ together form an aromatic or heteroaromatic ring having 5 or 6 ring members, which can be substituted by fluorine, chlorine, bromine or iodine atoms, alkyl($C_1$-$C_4$), acetamido, nitro or carboxyl groups, by reaction of aromatic compounds of the general formula II

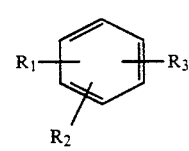

in which $R_1$, $R_2$ and $R_3$ have the abovementioned meanings, in a manner known per se with chlorosulfonic acid in excess or with chlorosulfonic acid or oleum and thionyl chloride, which comprises reacting in the presence of sulfamic acid as a catalyst.

The sulfamic acid employed according to the invention as a catalytically active auxiliary cannot be classified in any of the known compound classes of auxiliaries or catalysts for the sulfochlorination of aromatic compounds.

The aromatic sulfonyl chlorides are prepared from the aromatic compounds by methods known per se, for example by reaction of the aromatic compounds of the abovementioned general formula II with excess chlorosulfonic acid [cf. Winnacker-Kuchler, Chemische Technologie (Chemical Technology), volume 6, 4th edition, page 181, Carl-Hauser-Verlag Munich Vienna]or chlorosulfonic acid (or oleum) and thionyl chloride [DE 3,302,647].

In this connection, a procedure is expediently used in which the sulfamic acid is partially or completely added to the chlorosulfonic acid and, in the case of only partial addition at the beginning of the reaction, further sulfamic acid is metered in during the reaction.

However, it is also possible to convert the aromatic starting compound into the aromatic sulfonic acid first using chlorosulfonic acid or oleum, to add the sulfamic acid to the reaction mixture produced in this case and then to react further to give the arylsulfonyl chloride with thionyl chloride.

The sulfamic acid is expediently added in an amount of about 0.1 to about 20% by weight, preferably about 0.5 to about 5% by weight, relative to the aromatic compound of said general formula (II), to the chlorosulfonic acid, which is used in excess (when working without thionyl chloride), or after completion of the sulfonation in the first step and before addition of the thionyl chloride in the second step. Addition of sulfamic acid in larger amounts is admittedly possible, but possesses no advantages. As far as the temperatures are concerned, those in the known sulfochlorination of aromatic compounds with an excess of chlorosulfonic acid, i.e. temperatures of about −10° C. to about 150° C., preferably of about 20° C. to about 120° C., or those in the known sulfonation of aromatic compounds with chlorosulfonic acid or oleum in the first step, i.e. temperatures of about −10° C. to about 150° C., preferably of about 20° C. to about 130° C., and those in the subsequent known sulfochlorination with thionyl chloride in the second step, i.e. temperatures of about 30° C. to about 150° C., preferably about 50° C. to about 130° C., can be used.

The examples and comparison examples below are used to illustrate the process according to the invention without limiting it thereto.

EXAMPLE 1

4-Chlorobenzenesulfonyl chloride 112.6 g (1.0 mol) of chlorobenzene are added dropwise at 70° C. over a period of 1 hour to 122 g (1.05 mol)

of chlorosulfonic acid and 1 g of sulfamic acid. The mixture is then stirred at this temperature for 15 minutes.

180 g (1.5 mol) of thionyl chloride are then added dropwise at 70° C. over a period of 2 hours and the mixture is stirred until evolution of gas has ended. The excess thionyl chloride is distilled off and the residue is slowly added to ice water. The precipitated 4-chlorobenzenesulfonyl chloride is filtered off with suction and washed with ice water. 202.3 g of moist 4-chlorobenzenesulfonyl chloride having a water content of 4% are obtained. This corresponds to 194.2 g of 4-chlorobenzenesulfonyl chloride (9% of theory), calculated as dry material, having a purity of 95%.

EXAMPLE 2

4-Chlorobenzenesulfonyl chloride 112.6 g (1.0 mol) of chlorobenzene are added dropwise at 70° C. over a period of 1 hour to 122 g (1.05 mol) of chlorosulfonic acid. The mixture is then stirred at this temperature for 15 minutes. 1 g of sulfamic acid is then added and 180 g (1.5 mol) of thionyl chloride are added dropwise at 70° C. in the course of 2 hours. Working up is carried out as described in Example 1. 228.3 g of moist 4-chlorobenzenesulfonyl chloride having a water content of 12% are obtained. This corresponds to 200.9 g of 4chlorobenzenesulfonyl chloride (94.4% of theory), calculated as dry material, having a purity of 95%.

EXAMPLE 3 4-Chlorobenzenesulfonyl chloride

Comparison example without use of sulfamic acid

Comparison example without use of sulfamic acid 122 g (1.05 mol) of chlorosulfonic acid, 112.6 g (1.0 mol) of chlorobenzene and 180 g (1.5 mol) of thionyl chloride are reacted as described in Example 1, but without addition of sulfamic acid.

172.8 g of moist 4-chlorobenzenesulfonyl chloride having a water content of 7.1% are obtained. This corresponds to 160.5 g of 4-chlorobenzenesulfonyl chloride (76% of theory) having a purity of 94%.

EXAMPLES 4 TO 11

1 mol of an aromatic compound from Table 1 below is added dropwise at 70° C. to 1 mol of chlorosulfonic acid. The mixture is then stirred for 15 minutes. 1 g of sulfamic acid is then added first, as indicated in Table 1, after which 2 mol of thionyl chloride are added dropwise and finally the mixture is stirred until the evolution of gas has ended. For working up, the mixture is distilled.

The reaction without addition of sulfamic acid is also carried out for comparison.

TABLE 1

| Ex. No. | Aromatic Compound | Catalyst | b.p. | Yield (% of theory) | Purity (GC surface area %) |
|---|---|---|---|---|---|
| 4 | benzene | with | 142° C./40 torr | 88.9 | 98.3 |
| 5 | benzene | without | 142 C./40 torr | 78.6 | 98.3 |
| 6 | fluorobenzene | with | 124° C./8 torr | 84.8 | 97.0 |
| 7 | fluorobenzene | without | 124° C./8 torr | 76.0 | 96.9 |
| 8 | toluene | with | 110° C./2 torr | 89.9 | 76 p- 24 o- |
| 9 | toluene | without | 110° C./2 torr | 80.3 | 76 p- 24 o- |
| 10 | cumene | with | 136° C./2 torr | 85.8 | 96.7 |

TABLE 1-continued

| Ex. No. | Aromatic Compound | Catalyst | b.p. | Yield (% of theory) | Purity (GC surface area %) |
|---|---|---|---|---|---|
| 11 | cumene | without | 136° C./2 torr | 67.5 | 94.0 |

EXAMPLE 12

2-Nitrotoluene-4-sulfonyl chloride 137.1 g (1.0 mol) of o-nitrotoluene are added dropwise to 535.9 g (4.6 mol) of chlorosulfonic acid and 2 g of sulfamic acid such that the temperature does not exceed 40° C. The mixture is then stirred at 40° C. for 1 hour and slowly heated to 105° C. It is then stirred at 105° C. for 6 hours, cooled and added dropwise to ice water at 0 to 5° C. The precipitated crystals are filtered off with suction and washed with ice water. 236.1 g of 2-nitrotoluene-4-sulfonyl chloride (water content 10.8%), corresponding to 210.6 g (89% of theory), having a melting point of 40° C. are obtained.

EXAMPLE 13

2-Nitrotoluene-4-sulfonyl chloride

Comparison Example 535.9 g (4.6 mol) of chlorosulfonic acid are reacted with 137.1 g (1.0 mol) of o-nitrotoluene analogously to Example 12, but without sulfamic acid. Yield 200.7 g (water content 6.3%), corresponding to 188.1 g (80% of theory).

EXAMPLE 14

4-Acetamidobenzenesulfonyl chloride 135.2 g (1.0 mol) of acetanilide are added in portions to 349.5 g (3.0 mol) of chlorosulfonic acid and 2 g of sulfamic acid such that the temperature remains at 40° C. The mixture is then heated to 60° C. and stirred at this temperature for 60 minutes, then 142.8 g (1.2 mol) of thionyl chloride are added dropwise over the course of 2 hours and the mixture is stirred until evolution of gas has ended. For working up, the mixture is dripped into ice water, and the precipitated crystals are filtered off with suction and washed with water. 394.9 g of 4-acetamidobenzenesulfonyl chloride (water content: 41.7%; chloride content: 58.1%), corresponding to 230.2 g (98.5%) calculated as dry material, having a melting point of 139° C. are obtained.

EXAMPLE 15

4-Acetamidobenzenesulfonyl chloride

Comparison Example 135.2 g (1.0 mol) of acetanilide, 349.5 g (3.0 mol) of chlorosulfonic acid and 142.8 g (1.2 mol) of thionyl chloride are reacted analogously to Example 14, but without sulfamic acid. 358.5 g of 4-acetamidobenzenesulfonyl chloride (water content: 39.4%, chloride content: 60.2%), corresponding to 217.3 g (93.0% of theory), calculated as dry material, having a melting point of 139° C. are obtained.

EXAMPLE 16

3-Chlorosulfonylbenzoic acid 122.1 g (1.0 mol) of benzoic acid are introduced into a mixture of 349.5 g (3.0 mol) of chlorosulfonic acid, 20 g of 96% strength sulfuric acid and 1 g of sulfamic acid. The reaction mixture thus obtained is heated to 120° C. in the course of 3 hours and stirred until evolution of gas has ended. The mixture is then cooled to 70° C. and 119.0 g (1.0 mol) of thionyl chloride are added dropwise over the course of 2 hours. After it has been stirred at 80° C. for 30 minutes, the reaction mixture is added dropwise at 10° C. to ice water, and the precipitated crystals are filtered off with suction and washed with ice water. 232.1 g of 3-chlorosulfonylbenzoic acid (water content: 10%), corresponding to 208.9 g (94.7% of theory), calculated as dry material, having a melting point of 129°-131° C. are obtained.

EXAMPLE 17

3-Chlorosulfonylbenzoic acid

Comparison Example 122.1 g (1.0 mol) of benzoic acid, 349.5 g (3.0 mol) of chlorosulfonic acid, 20 g of 96% strength sulfuric acid and 119 g (1.0 mol) of thionyl chloride are reacted analogously to Example 16, but without addition of sulfamic acid. 198.3 g of 3-chlorosulfonylbenzoic acid (water content: 8.2%), corresponding to 182.0 g (82.5% of theory), calculated as dry material, are obtained.

EXAMPLE 18

6-Benzoxazolonesulfonyl chloride 135 g (1.0 mol) of benzoxazolone are introduced into 349.5 g (3.0 mol) of chlorosulfonic acid and 1 g of sulfamic acid in such a way that the temperature does not rise above 40° C. The mixture is then heated to 60° C. and stirred at this temperature for 1 hour. 142.8 g (1.2 mol) of thionyl chloride are then added dropwise and the mixture is stirred until the evolution of gas is complete. The reaction mixture is dripped into ice water, and the precipitated crystals are filtered off with suction and washed with water. 264.2 g of moist 6-benzoxazolibe sulfonyl chloride having a water content of 21.2% and a melting point of 188°-190° C., corresponding to a yield of 208.5 g (89.3% of theory), are obtained.

EXAMPLE 19

6-Benzoxazolonesulfonyl chloride

Comparison Example 349.5 g (3.0 mol) of chlorosulfonic acid, 135 g (1.0 mol) of benzoxazolone and 142.8 g (1.2 mol) of thionyl chloride are reacted as described in Example 18, but without addition of sulfamic acid.

231.7 g of 6-benzoxazolonesulfonyl chloride having a water content of 19.4%, corresponding to a yield of 186.8 g (80.0% of theory), are obtained.

EXAMPLE 20

3-Nitrobenzenesulfonyl chloride 123.1 g (1.0 mol) of nitrobenzene are allowed to run rapidly into 582.5 g (5.0 mol) of chlorosulfonic acid and 1 g of sulfamic acid at room temperature. The mixture is then heated to 105° C. and stirred at this temperature for 6 hours. For working up, the reaction mixture is dripped into ice water. The precipitated crystals are filtered off with suction and washed with water. 194.6 g of dry 3-nitrobenzenesulfonyl chloride having a melting point of 59°-61° C., corresponding to a yield of 87.8% of theory, are obtained.

EXAMPLE 21 3-Nitrobenzenesulfonyl chloride

Comparison Example 123.1 g (1.0 mol) of nitrobenzene and 582.5 g (5.0 mol) of chlorosulfonic acid are reacted as described in Example 20, but without addition of sulfamic acid. 175.1 g of dry 3-nitrobenzenesulfonyl chloride, corresponding to a yield of 79.0% of theory, are obtained.

EXAMPLE 22

2-Nitrochlorobenznen-4-sulfonyl chloride 157.6 g (1.0 mol) of 2-chloronitrobenzene are added to 699 g (6.0 mol) of chlorosulfonic acid and 2 g of sulfamic acid such that the temperature does not exceed 40° C. After addition is complete, the mixture is heated to 100° C. and stirred at this temperature for 6 hours. The reaction mixture is dripped into water at 15° C., and the precipitated crystals are filtered off with suction and washed with water. 236.2 g of 2-nitrochlorobenzene-4-sulfonyl chloride having a water content of 1.5%, corresponding to 232.7 g of 2-nitrochlorobenzene-4-sulfonyl chloride (90.8% of theory), are obtained.

EXAMPLE 23

2-Nitrochlorobenzene-4-sulfonyl chloride

Comparison Example 157.6 g (1.0 mol) of 2-chloronitrobenzene and 699 g (6.0 mol) of chlorosulfonic acid are reacted as in Example 22, but without addition of sulfamic acid. 212.8 g of 2-nitrochlorobenzene-4-sulfonyl chloride having a water content of 1.2%, corresponding to 210.2 g of 2-nitrochlorobenzene-4-sulfonyl chloride (82.1% of theory), are obtained.

EXAMPLE 24

Naphthalene-1,5-disulfonyl chloride 64.1 g (0.5 mol) of naphthalene are introduced with ice cooling into 640.7 g (5.5 mol) of chlorosulfonic acid, to which 1 g of sulfamic acid has been added. The mixture is then stirred at room temperature for 4 hours. The reaction mixture is added dropwise to ice water, and the precipitated crystals are filtered off with suction and washed with water. 172.1 g of naphthalene-1,5-disulfonyl chloride having a water content of 26.5% and a chloride content of 71.6%, corresponding to 123.2 g (75.7%), are obtained.

EXAMPLE 25

Naphthalene-1,5-disulfonyl chloride

Comparison Example 64.1 g (0.5 mol) of naphthalene and 640.7 g (5.5 mol) of chlorosulfonic acid are reacted as in Example 26, but without addition of sulfamic acid. 139.4 g of naphthalene-1,5-disulfonyl chloride having a water content of 25.8% and a chloride content of 72.5%, corresponding to 101.1 g (62.2%), are obtained.

We claim:

1. A process for the preparation of aromatic sulfonyl chlorides of the formula I

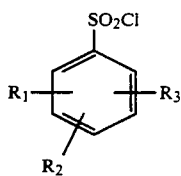

(I)

in which $R_1$, $R_2$ and $R_3$ are identical or different and are hydrogen, fluorine, chlorine, bromine or iodine atoms, alkyl ($C_1$–$C_4$), acetamido, nitro or carboxyl groups, or $R_1$ and $R_2$ together form an aromatic ring having 5 to 6 ring members or form an oxazolone ring which comprises reacting aromatic compounds of the formula II

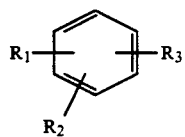

(II)

in which $R_1$, $R_2$ and $R_3$ have the abovementioned meanings, with chlorosulfonic acid in excess or with chlorosulfonic acid or oleum and thionyl chloride in the presence of about 0.1 to about 20% by weight of sulfamic acid relative to the aromatic compound of said formula II as a catalyst at a temperature in the range of from −10 to 150° C.

2. The process as claimed in claim 1, which comprises reacting in the presence of about 0.5 to about 5% by weight of sulfamic acid, relative to the aromatic compound of said formula II.

3. The process as claimed in claim 1, which process is carried out at normal or elevated pressure.

4. The process as claimed in claim 1, wherein the sulfamic acid is completely added to the chlorosulfonic acid at the start of the reaction.

5. The process as claimed in claim 1, wherein the sulfamic acid is only partially added to the chlorosulfonic acid at the start of the reaction and further sulfamic acid is metered in during the course of the reaction.

6. The process as claimed in claim 1, wherein, when using chlorosulfonic acid or oleum as the sulfonating agent, the sulfamic acid is added to the reaction mixture obtained after reaction of the aromatic compound of said formula II with said sulfonating agent and the mixture is then reacted with thionyl chloride to give arylsulfonyl chloride.

* * * * *